(12) United States Patent
Yeung et al.

(10) Patent No.: US 9,789,613 B2
(45) Date of Patent: Oct. 17, 2017

(54) MAGNETIC-ANCHORED ROBOTIC SYSTEM

(71) Applicant: Bio-Medical Engineering (HK) Limited, Hong Kong (CN)

(72) Inventors: Chung Kwong Yeung, Hong Kong (CN); Kai Leung Yung, Hong Kong (CN)

(73) Assignee: BIO-MEDICAL ENGINEERING (HK) LIMITED, Hong Kong (CN)

( * ) Notice: Subject to any disclaimer, the term of this patent is extended or adjusted under 35 U.S.C. 154(b) by 92 days.

(21) Appl. No.: 13/835,653

(22) Filed: Mar. 15, 2013

(65) Prior Publication Data

US 2013/0289579 A1    Oct. 31, 2013

Related U.S. Application Data

(60) Provisional application No. 61/638,828, filed on Apr. 26, 2012, provisional application No. 61/718,252, filed on Oct. 25, 2012.

(51) Int. Cl.
*B25J 13/08* (2006.01)
*A61B 17/00* (2006.01)
(Continued)

(52) U.S. Cl.
CPC ............. *B25J 13/088* (2013.01); *A61B 17/00* (2013.01); *A61B 17/00234* (2013.01);
(Continued)

(58) Field of Classification Search
CPC ....... A61B 19/20; A61B 19/201; A61B 19/22;
A61B 19/2203; A61B 2019/2207; A61B 2019/2215; A61B 2019/2253; A61B 2019/2257; A61B 2019/5227; A61B 17/00234; A61B 17/00; A61B 17/3423;
(Continued)

(56) References Cited

U.S. PATENT DOCUMENTS 4,278,077 A   7/1981   Mizumoto
5,604,531 A   2/1997   Iddan et al.
(Continued)

FOREIGN PATENT DOCUMENTS

CN   101091665   12/2007
JP   2004321692  11/2004
(Continued)

OTHER PUBLICATIONS

International Search Report and Written Opinion dated PCT/CN2013/000478 dated Jul. 25, 2013, nine pages.
(Continued)

*Primary Examiner* — Jocelin Tanner
(74) *Attorney, Agent, or Firm* — Baker & McKenzie LLP

(57) ABSTRACT

A surgical system includes an external anchor, an internal anchor and an instrument. The external anchor is adapted to be positioned outside a body. The internal anchor is adapted to be inserted into the body via a single entrance port, positioned inside the body and magnetically coupled with the external anchor. The instrument is adapted to be inserted into the body via the single entrance port and secured to the internal anchor. The instrument includes an end-effector that has multiple degrees of movement via multiple axes.

5 Claims, 16 Drawing Sheets

(51) Int. Cl.
*A61B 34/00* (2016.01)
*A61B 17/34* (2006.01)
*A61B 34/30* (2016.01)
*A61B 90/00* (2016.01)

(52) U.S. Cl.
CPC .......... *A61B 17/3417* (2013.01); *A61B 34/30* (2016.02); *A61B 34/73* (2016.02); *A61B 34/76* (2016.02); *A61B 17/3423* (2013.01); *A61B 2017/00283* (2013.01); *A61B 2017/00876* (2013.01); *A61B 2017/3484* (2013.01); *A61B 2034/302* (2016.02); *A61B 2090/371* (2016.02); *Y10S 901/09* (2013.01); *Y10S 901/34* (2013.01); *Y10S 901/41* (2013.01); *Y10T 428/13* (2015.01)

(58) Field of Classification Search
CPC ... A61B 2017/3484; A61B 2017/00283; B25J 13/088; Y10T 428/13; Y10S 901/09; Y10S 901/34; Y10S 901/41
USPC ...... 606/130; 901/46, 9, 15, 28; 318/568.11, 318/560, 568.21, 568.22; 600/427, 104, 600/118, 117, 12, 184, 114, 145, 201; 607/1
See application file for complete search history.

(56) References Cited

U.S. PATENT DOCUMENTS

| | | | |
|---|---|---|---|
| 6,240,312 B1 | 5/2001 | Alfano et al. | |
| 6,402,686 B1 | 6/2002 | Ouchi | |
| 6,648,814 B2 | 11/2003 | Kim et al. | |
| 6,702,734 B2 | 3/2004 | Kim et al. | |
| 6,719,684 B2 | 4/2004 | Kim et al. | |
| 6,776,165 B2 | 8/2004 | Jin | |
| 6,936,003 B2 | 8/2005 | Iddan | |
| 6,984,205 B2 | 1/2006 | Gazdzinski | |
| 6,991,627 B2 | 1/2006 | Madhani et al. | |
| 7,039,453 B2 | 5/2006 | Mullick et al. | |
| 7,042,184 B2 | 5/2006 | Oleynikov et al. | |
| 7,066,879 B2 | 6/2006 | Fowler et al. | |
| 7,126,303 B2 | 10/2006 | Farritor et al. | |
| 7,169,104 B2 | 1/2007 | Ueda et al. | |
| 7,182,089 B2 | 2/2007 | Ries | |
| 7,199,545 B2 | 4/2007 | Oleynikov et al. | |
| 7,311,107 B2 | 12/2007 | Harel et al. | |
| 7,339,341 B2 | 3/2008 | Oleynikov et al. | |
| 7,429,259 B2 | 9/2008 | Cadeddu et al. | |
| 7,492,116 B2 | 2/2009 | Oleynikov et al. | |
| 7,625,338 B2 | 12/2009 | Gilad et al. | |
| 7,691,103 B2 | 4/2010 | Fernandez et al. | |
| 8,145,295 B2 | 3/2012 | Boyden et al. | |
| 8,343,171 B2 | 1/2013 | Farritor et al. | |
| 2002/0103417 A1 | 8/2002 | Gazdzinski | |
| 2003/0020810 A1 | 1/2003 | Takizawa et al. | |
| 2003/0092964 A1 | 5/2003 | Kim et al. | |
| 2003/0100892 A1* | 5/2003 | Morley ............... | A61B 17/062 606/1 |
| 2003/0114731 A1 | 6/2003 | Cadeddu et al. | |
| 2003/0167000 A1 | 9/2003 | Mullick et al. | |
| 2004/0050395 A1* | 3/2004 | Ueda et al. .................. | 128/899 |
| 2004/0176664 A1 | 9/2004 | Iddan | |
| 2005/0029978 A1 | 2/2005 | Oleynikov | |
| 2005/0096502 A1 | 5/2005 | Khalili | |
| 2005/0165449 A1 | 7/2005 | Cadeddu et al. | |
| 2005/0273139 A1 | 12/2005 | Krauss et al. | |
| 2005/0288555 A1 | 12/2005 | Binmoeller | |
| 2006/0009785 A1* | 1/2006 | Maitland et al. ............. | 606/113 |
| 2006/0119304 A1 | 6/2006 | Farritor et al. | |
| 2006/0149135 A1 | 7/2006 | Paz | |
| 2006/0190034 A1* | 8/2006 | Nishizawa et al. ........... | 606/205 |
| 2006/0196301 A1 | 9/2006 | Oleynikov et al. | |
| 2006/0198619 A1 | 9/2006 | Oleynikov et al. | |
| 2007/0032701 A1 | 2/2007 | Fowler | |
| 2007/0080658 A1 | 4/2007 | Farritor et al. | |
| 2007/0123748 A1 | 5/2007 | Meglan | |
| 2007/0157937 A1 | 7/2007 | Mikkaichi et al. | |
| 2007/0161855 A1* | 7/2007 | Mikkaichi et al. ........... | 600/113 |
| 2007/0241714 A1 | 10/2007 | Okeynikov et al. | |
| 2007/0255273 A1* | 11/2007 | Fernandez et al. ............. | 606/41 |
| 2008/0004634 A1 | 1/2008 | Farritor et al. | |
| 2008/0058835 A1 | 3/2008 | Farritor et al. | |
| 2008/0058989 A1 | 3/2008 | Oleynikov et al. | |
| 2008/0111513 A1 | 5/2008 | Farritor et al. | |
| 2008/0221591 A1 | 9/2008 | Farritor et al. | |
| 2008/0249359 A1 | 10/2008 | Abraham-Fuchs et al. | |
| 2008/0269779 A1 | 10/2008 | Cadeddu et al. | |
| 2009/0048612 A1 | 2/2009 | Farritor et al. | |
| 2009/0054909 A1 | 2/2009 | Farritor et al. | |
| 2009/0069821 A1 | 3/2009 | Farritor et al. | |
| 2009/0171373 A1 | 7/2009 | Farritor et al. | |
| 2009/0259340 A1 | 10/2009 | Umemoto et al. | |
| 2010/0114126 A1* | 5/2010 | Neff .............................. | 606/151 |
| 2010/0256636 A1 | 10/2010 | Fernandez et al. | |
| 2010/0318059 A1 | 12/2010 | Farritor et al. | |
| 2011/0087223 A1 | 4/2011 | Spivey | |
| 2011/0087224 A1 | 4/2011 | Cadeddu et al. | |
| 2011/0224605 A1 | 9/2011 | Farritor et al. | |
| 2011/0237890 A1 | 9/2011 | Farritor et al. | |
| 2011/0283822 A1 | 11/2011 | Cadeddu et al. | |
| 2011/0284014 A1 | 11/2011 | Cadeddu et al. | |
| 2011/0285488 A1 | 11/2011 | Scott et al. | |
| 2011/0313415 A1 | 12/2011 | Fernandez et al. | |
| 2012/0035416 A1 | 2/2012 | Fernandez et al. | |
| 2012/0065627 A1 | 3/2012 | Ghabrial et al. | |
| 2012/0179168 A1 | 7/2012 | Farritor et al. | |
| 2013/0041360 A1 | 2/2013 | Farritor et al. | |

FOREIGN PATENT DOCUMENTS

| | | |
|---|---|---|
| JP | 2005028006 | 2/2005 |
| WO | 2007149559 | 12/2007 |
| WO | 2008103212 | 8/2008 |
| WO | 2009014917 | 1/2009 |
| WO | 2009023851 | 2/2009 |
| WO | 2010083480 | 7/2010 |
| WO | 2011044468 | 4/2011 |
| WO | 2011075693 | 6/2011 |
| WO | 2012035157 | 3/2012 |

OTHER PUBLICATIONS

International Search Report and Written Opinion dated PCT/CN2013/000480 dated Aug. 8, 2013, eleven pages.

* cited by examiner

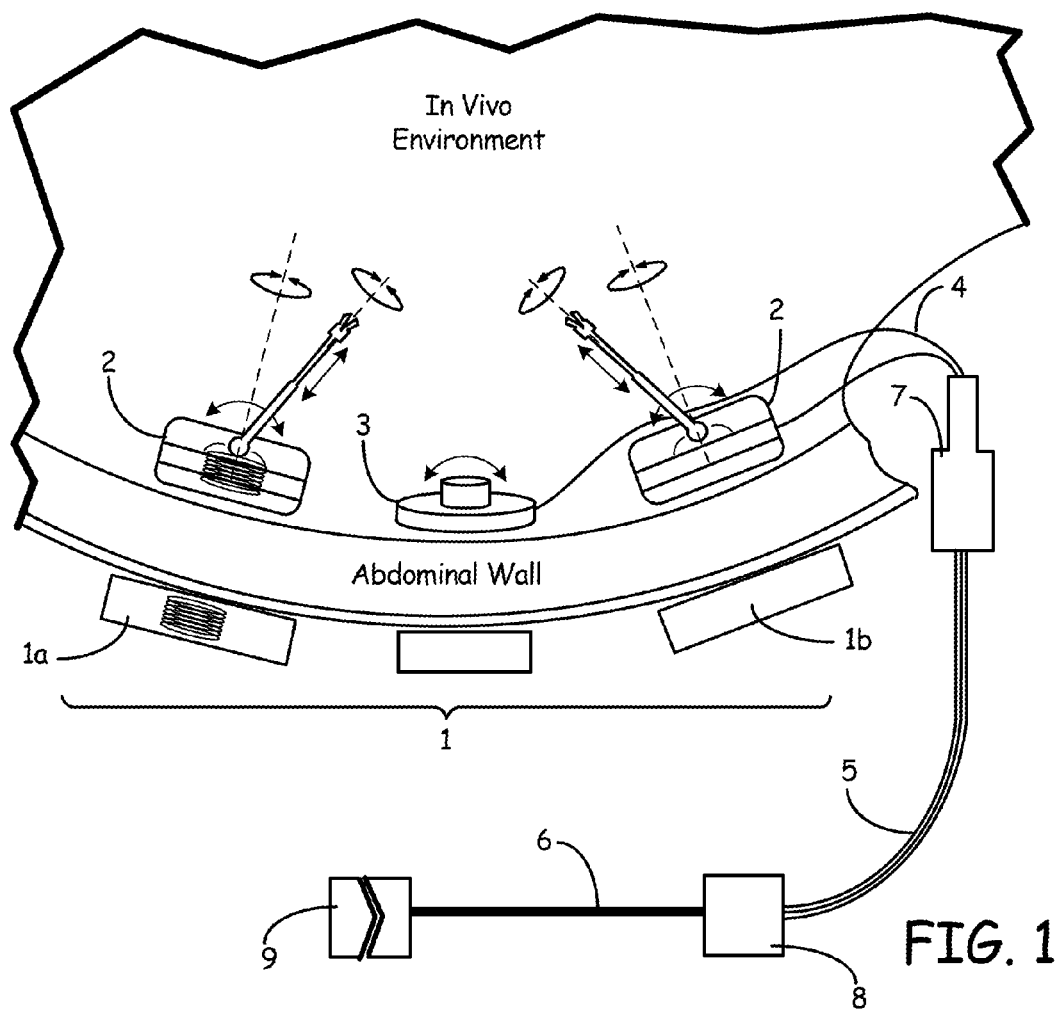
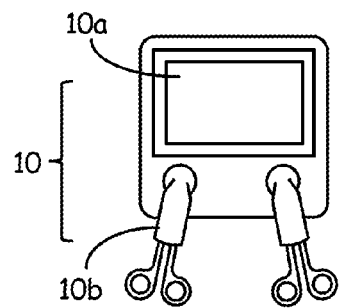
FIG. 1A
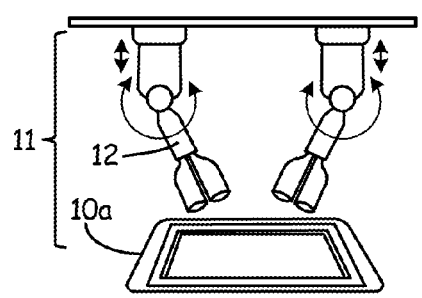
FIG. 1B

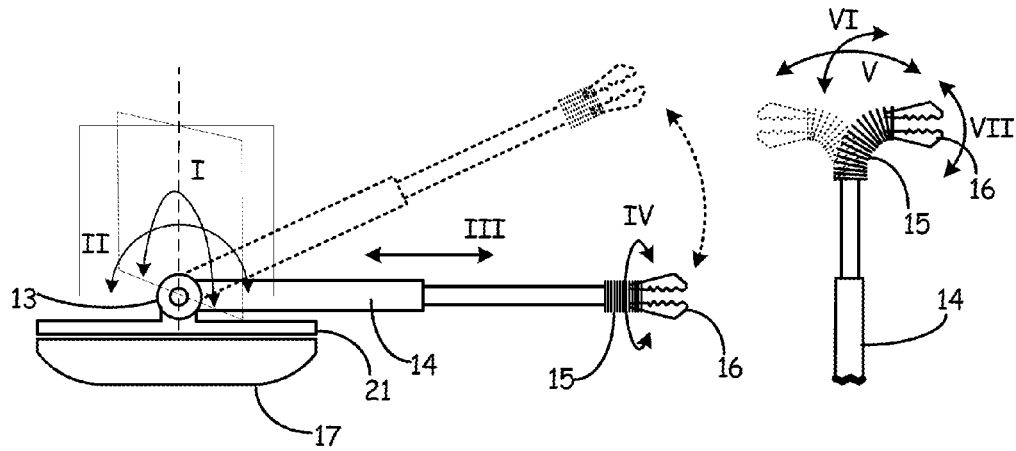
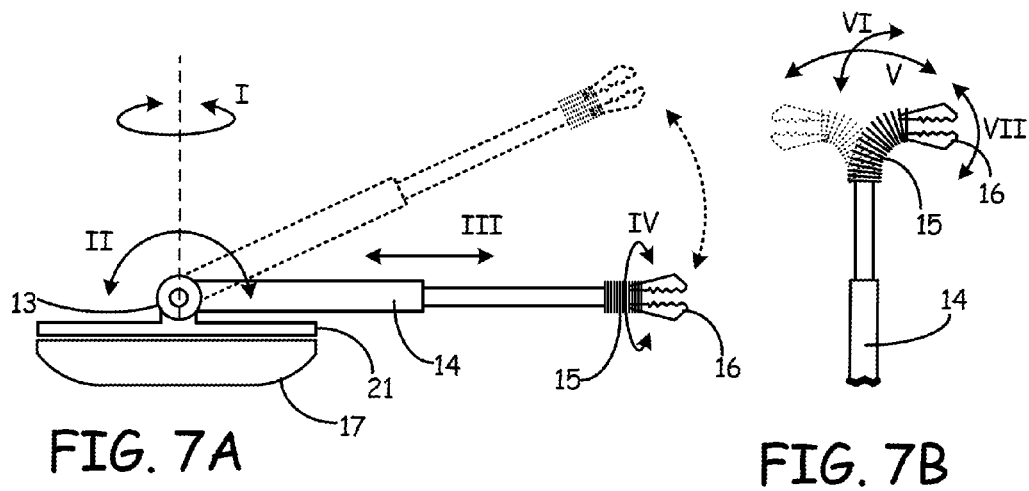
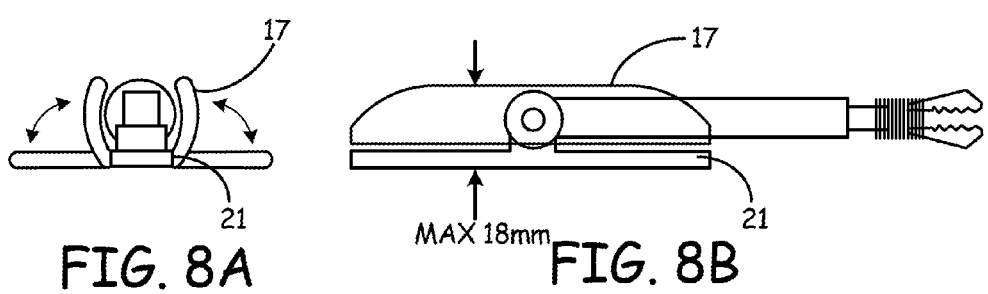

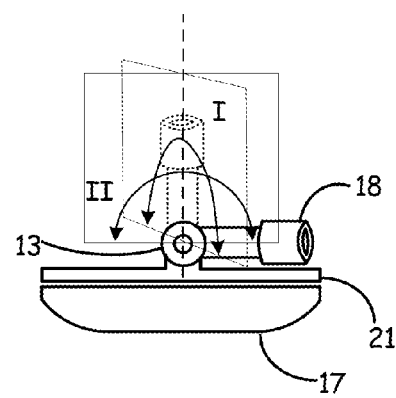
FIG. 9
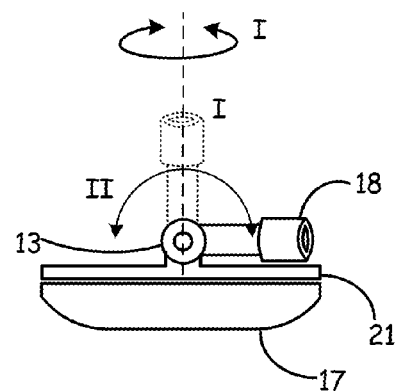
FIG. 10
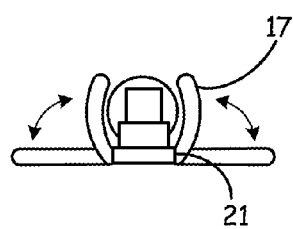 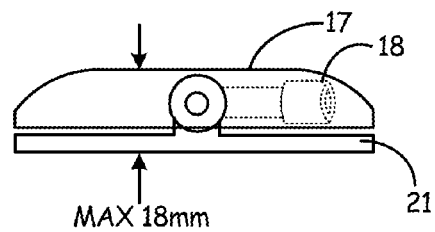
FIG. 11A          FIG. 11B

MAGNETIC-ANCHORED ROBOTIC SYSTEM

CROSS-REFERENCE TO RELATED APPLICATIONS

This application claims priority to U.S. Provisional App. Ser. No. 61/638,828, filed Apr. 26, 2012 and U.S. Provisional App. Ser. No. 61/718,252, filed Oct. 25, 2012, each of which is hereby incorporated by reference in its entirety. This application is related to U.S. application Ser. No. 13/835,680, now U.S. Pat. No. 8,891,924, titled "Magnetic-Anchored Robotic System" and filed on even date.

BACKGROUND

Surgeons have traditionally depended on external illumination from the operating room light and adequate exposure to obtain a good surgical view. This often requires large incisions, especially if the surgeon has larger hands, to provide access for the operation. The introduction of fiber optics in modern endoscopes has allowed surgeons to see clearly with good illumination inside a bodily cavity without having to make a big incision. Minimally Invasive Surgery (MIS) has now replaced most conventional open surgical operations. Computer-assisted or robotic technology has contributed further to the development of MIS as the computer sensors of the robotic machine can reliably and delicately translate the movements of the surgeon's fingers and wrists into movements of the slave laparoscopic instruments inside the body cavities. These developments have allowed good dexterity and precision control of surgical instruments for fine reconstructive surgery in a small confined space.

However, the MIS approach requires multiple incisions for the insertion of the camera and various laparoscopic instruments. Over the past few years, Laparo-Endoscopic Single-Site (LESS) surgery technologies have become available, but these suffer immensely from a lack of proper triangulation between the camera and the working instruments, which is important for good operative ergonomics and hence ease and success of surgery.

Natural orifice translumenal endoscopic surgery (NOTES) is an alternative to open abdominal surgery that uses endoscopic techniques with a view to completely avoid the need for external abdominal wall incisions. Theoretically, NOTES offers advantages by minimizing access trauma and the various complications associated with external incisions including wound infections, pain, hernia formation, unsightly abdominal scars and adhesions.

However, the NOTES approach suffers from significant drawbacks including inadequacy of proper triangulation of surgical instruments and hence poor working ergonomics, an inability to apply off-axis forces, and difficulties in passing multiple instruments into the abdominal cavity for proper surgical manipulations.

BRIEF SUMMARY

In an embodiment, a surgical system includes an external anchor, an internal anchor and an instrument. The external anchor is adapted to be positioned outside a body. The internal anchor is adapted to be inserted into the body via a single entrance port, positioned inside the body and magnetically coupled with the external anchor. The instrument is adapted to be inserted into the body via the single entrance port and secured to the internal anchor. The instrument includes an end-effector and a foldable enclosure. The end-effector has multiple degrees of movement via multiple axes. The foldable enclosure has at least a first and second configuration. The first configuration provides the enclosure in a folded state adapted for insertion into the body. The second configuration provides the enclosure in an unfolded state.

In another embodiment, a surgical system includes an external anchor, an internal anchor, an instrument and a wire. The external anchor is adapted to be positioned outside a body. The internal anchor is adapted to be inserted into the body via a single entrance port, positioned inside the body and magnetically coupled with the external anchor. The instrument is adapted to be inserted into the body via the single entrance port and secured to the internal anchor. The instrument includes an end-effector having multiple degrees of movement via multiple axes. The external anchor includes an aperture through which the wire can pass.

In another embodiment, a surgical system, includes an external anchor, an internal anchor, an instrument and a flexible magnetic sheet. The external anchor is adapted to be positioned outside a body. The internal anchor is adapted to be inserted into the body via a single entrance port, positioned inside the body and magnetically coupled with the external anchor. The instrument is adapted to be inserted into the body via the single entrance port and secured to the internal anchors. The instrument includes an end-effector having multiple degrees of movement via multiple axes. The flexible magnetic sheet is adapted for insertion into the body via the single entrance port.

In another embodiment, a surgical method includes inserting at least two internal anchors and instruments into a body through a single entrance port, the instruments being securable to the internal anchors and each including an end-effector having multiple degrees of movement via multiple axes; reconfiguring the internal anchors from insertion configurations to operation configurations, the operation configurations respectively having a larger contact area with a wall of the body than the insertion configurations; and positioning at least one external anchor outside the body such that the internal anchors and the external anchor are magnetically coupled across the wall of the body.

BRIEF DESCRIPTION OF THE DRAWINGS

FIG. 1 is a general schematic view of an exemplary surgical robotic system.

FIGS. 1A and 1B are front views of exemplary human-machine interfaces.

FIGS. 6A and 6B are side views showing 7-axis movement of an exemplary micro robotic manipulator.

FIGS. 7A and 7B are side views showing 7-axis movement of an exemplary micro robotic manipulator.

FIG. 8A is an end view and FIG. 8B is a side view of an exemplary foldable enclosure of a micro robotic manipulator.

FIG. 9 is a side view showing 2-axis movement of an exemplary 2D micro robotic camera.

FIG. 10 is a side view showing 2-axis movement of an exemplary 2D micro robotic camera.

FIG. 11A is an end view and FIG. 11B is a side view of an exemplary foldable enclosure of a micro robotic 2D-camera.

DETAILED DESCRIPTION

A Magnetic-anchored Robotic System (MRS) allows computer-assisted minimally-invasive surgery using multiple independent in-vivo miniature robots that can have a full seven-degrees of freedom of movement in different axis (note that in addition to the degrees of freedom of movement of the miniature robots discussed below, two more degrees of freedom are available by translating the miniature robots along the abdominal wall). Intra-abdominal operations can be performed under the surveillance of an in-vivo swivel camera under remote control by the surgeon through an external computer console. Each of the miniature robotic instruments, camera and other devices may be inserted into the abdominal cavity via either a single incision (for example, through the umbilicus) or through a natural orifice and may be secured into position by an external electro-magnetic anchoring and positioning device outside the abdominal wall at selected sites to provide operative ergonomics and triangulation between camera and instruments. The control of such miniature robotic system inside the abdominal cavity can be, for example, via a wired or a hybrid combination of wired and wireless communications, depending on the situation and the condition of the patient. In some arrangements, power will be transmitted to the miniature robotic instruments (effectors), by a pair of conductors, while the control signals of the same can be transmitted by wire or wirelessly.

The camera as well as all laparoscopic instruments can be inserted into the abdominal cavity through a single incision or through a natural orifice. The laparoscopic instruments can then be anchored and positioned through an external electro-magnet placed outside the abdominal wall. MRS can therefore allow MIS to be performed with the benefits of both computer-assisted or robotic surgery, as well as using either only a single incision or through a natural orifice (NOTES). An exemplary MRS may include:

(i) one or more externally-mounted electro-magnetic anchoring and positioning devices;

(ii) multiple internal electro-magnetic anchoring devices, each fitted with an independent miniature robotic surgical instrument capable of, for example, seven-degrees freedom of movements via multiple axis; and (iii) a surgeon's computer console that provides surgical control and manipulation.

Thus, exemplary advantages including minimized access trauma, provision of unrestricted or less restricted and more dexterous movement of instruments inside the cavity and enabling proper or improved triangulation of instruments for optimal or improved operative ergonomics can be achieved.

Figure 17:
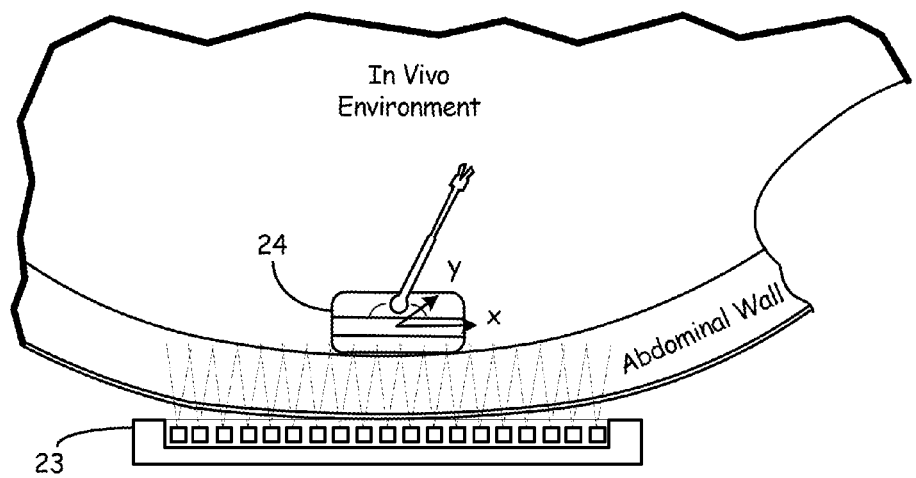
FIG. 17 is a side view of an exemplary micro robotic manipulator in an in vivo environment.
Figures 18A, 18B:
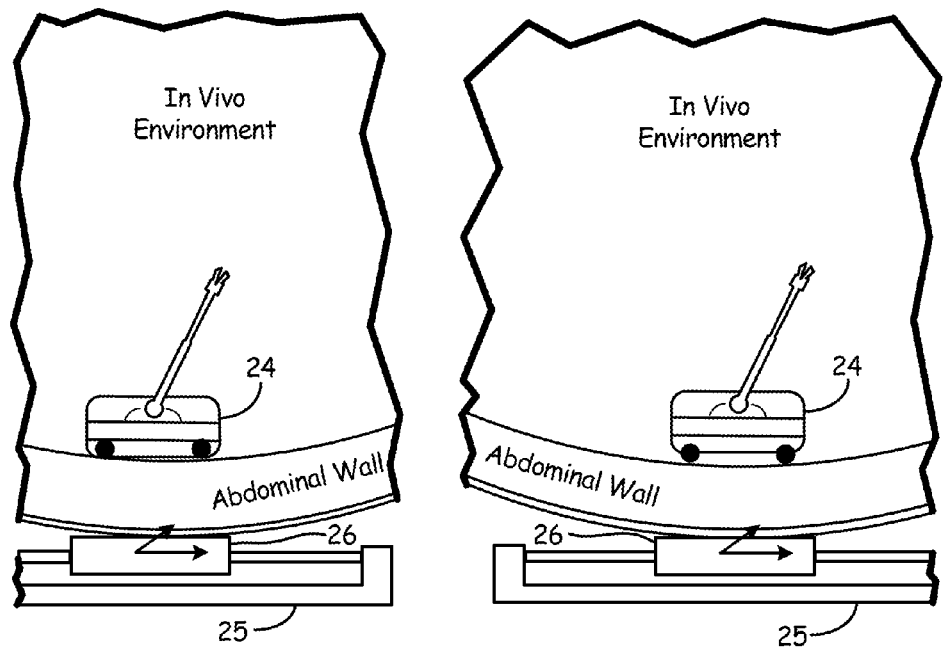
FIGS. 18A and 18B are side views of an exemplary micro robotic manipulator in an in vivo environment.

Referring to FIG. 1, the system may include one or more magnetic or electromagnetic location fixing device(s) 1 (hereafter collectively referred to as the electromagnetic location fixing device 1, which includes examples including permanent/non-electric magnets unless otherwise specifically excluded) placed on the outer abdominal wall associated with remotely controlled robotic manipulator(s) 2 inside the body. The electromagnetic location fixing device 1 may include a servo mechanism that is remotely controlled to control the position of the internal electromagnetic anchoring device. The robotic manipulator inside the human body can therefore be moved and be positioned by an externally supplied magnetic field interacting with one or more permanent magnets or electromagnets included in the electromagnetic location fixing device 1 together with the internal electromagnetic anchoring device. Such an externally supplied magnetic field may be moved by a X-Y servo mechanism to a designated position thus relocating the robotic arm 24 to the designated position and then refix again as shown in FIG. 18. As another example, the electromagnetic location fixing device 23 shown in FIG. 17 may be in the form of a linear induction stator on the outside of the abdominal wall such that when an alternating current of appropriate frequency is applied to the stator on the outside of the abdominal wall, the inside flap 24 will levitate and move forward. When such an alternating current is applied in pulse form, the inside flap 24 will move forward in small steps. Such control may also be provided by a control computer.

For illustrative purposes, each location fixing device is shown with one robotic manipulator; however, there may be multiple robotic manipulators for one location fixing device or multiple location fixing devices for one robotic manipulator. For example, each device may detect the current position of the end effector of the corresponding multi-axis micro robotic manipulator 2 inside the human body. The multi-axis micro robotic manipulator 2 inside the body may detect the current position of the end effector. The micro robotic manipulator 2 may include various end effectors such as a gripping device 16 (for example, as shown in FIG. 6) and an imaging device 3 for performing a given treatment and visualizing the in vivo environment respectively.

The manipulator 2 can be folded and inserted into the body cavity through an entrance port 7 in the form of a hollow cylinder mounted on a minimal invasive opening or the like of the patient. It may be connected to a flexible cable 4 passing through the entrance port 7 and linked to a central control computer 8 via an electrical wire 5 or wirelessly. The entrance port 7 is in the range of 1.5-2 cm in diameter in some examples but may vary. The range of 1.5-2 cm is advantageous as it is big enough for equipment (manipulators, etc) to pass through and small enough to be accommodated by most natural orifices.

Figure 2A:
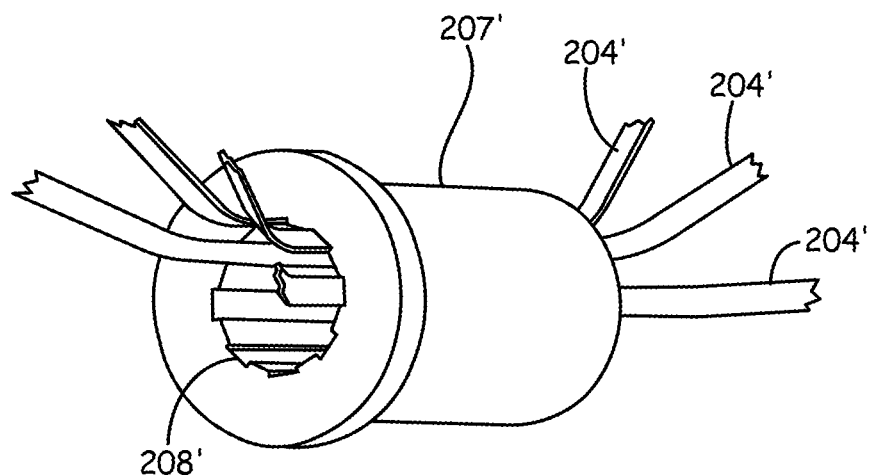
FIGS. 2A and 2B are perspective views of exemplary entrance ports.
Figure 2B:
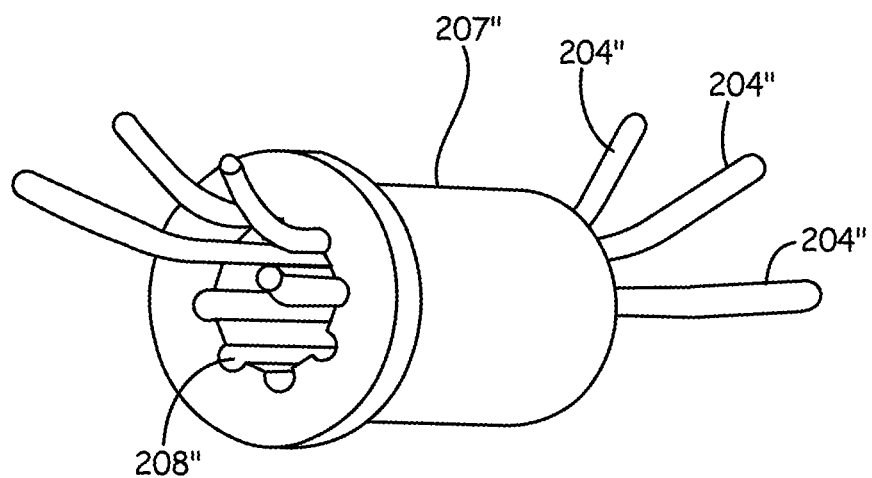

Referring to FIGS. 2A and 2B, the entrance ports 207' and 207" may be shaped to accommodate flexible cables 204' and 204" in a manner that permits multiple of the manipulators 2 to be inserted through the same single entrance port 207. An inner wall of the entrance ports 207' and 207" includes one or more recesses of a shape complementary to the wires 204' and 204".

In the example shown in FIG. 2A, the recesses 208' in the inner wall of the entrance port 207' are slot shaped and include a flat surface to accommodate the flat cable 204'. In some examples, a cross section of the inner wall may be in the shape of a polyhedron having the recesses 208' immediately joining an adjacent recess 208'. In other examples, the recesses 208' may be distributed circumferentially about the inner surface of the entrance port 207'. The recesses 208' may be distributed equally or unequally about the inner surface of the entrance port 207'.

In the example shown in FIG. 2B, the recesses 208" in the inner wall of the entrance port 207" are rounded to accommodate the round cable 204". In some examples, the recesses 208" immediately join an adjacent recess 208". In other examples, the recesses 208" may be distributed circumferentially about the inner surface of the entrance port 207". The recesses 208" may be distributed equally or unequally about the inner surface of the entrance port 207".

It will be appreciated that the above described shapes are exemplary in nature and can be selected form a variety of other shapes according to a particular implementation. Providing the recesses 208 allows for the use of the same entrance port for many of the manipulators 2 by clearing the opening of the entrance port 207 of the cables 204 to allow passage of another manipulator 2. In this way, trauma associated with the insertion of entrance ports, trocars, etc, can be minimized by reusing the same single entrance port for several or all of the manipulators 2.

Depending on the application, the signal transmission between the remotely controlled micro robotic manipulator 2 and the central control computer 8 can be performed through a wired connection (for example, via the entrance port 7 over a conductive cable or an optical cable) or a wireless connection (for example, via inductive coupling with a pickup coil incorporated in the location fixing device as shown in device 1*a*). Power for the manipulator 2 may also be supplied via the location fixing device 1 wirelessly through the abdominal wall. A hybrid such as a wired power supply and wireless control signal may also be used.

Also, in cases where the electromagnetic location fixing device 1 is controllable by the central control computer 8, a wired or wireless connection may be provided from the central control computer 8 to the electromagnetic location fixing device 1. Alternatively, or in addition, electromagnetic location fixing device 1 may communicate wirelessly with the micro robotic manipulator 2, which is connected to the central control computer 8 through a wired connection, for example via the entrance port 7, to provide communication between the electromagnetic location fixing device 1 and the central control computer 8. The central control computer 8 may control positioning servos of the electromagnetic location fixing device 1 as well as activating/deactivating a fixing control. The fixing control may be, for example, activating an electromagnet in the electromagnetic fixing device 1. The fixing control is not necessarily a discrete on/off control and may also be variable.

The central control computer 8 can adjust the positions and actions of the manipulators 2 independently of each other by the corresponding movement of the trigger unit 10*b*, 11*b* controlled by an operator through a human machine interface 9 connecting to the controller via a cable 6. The interface 9 may include a display screen 10*a*, 11*a* and a pair of trigger units 10*b*, 11*b*, which may be different types such as the remote operation type 10 shown in FIG. 1A and multi-axis end-effector simulator type 11 shown in FIG. 1B. In the multi-axis end-effector simulator type 11, the trigger unit 11*b* has a multi-axis robotic joint that can provide fine position control of the end effector of the manipulator 2 with several degrees of freedom. The movement control can also include force feedback.

Also, the number of inserted miniature robots is not limited to the number that can be controlled by one operator through the human machine interface 9. A second human machine interface may be provided for an assistant operator to also control miniature robots if needed for the operation.

Figure 3:
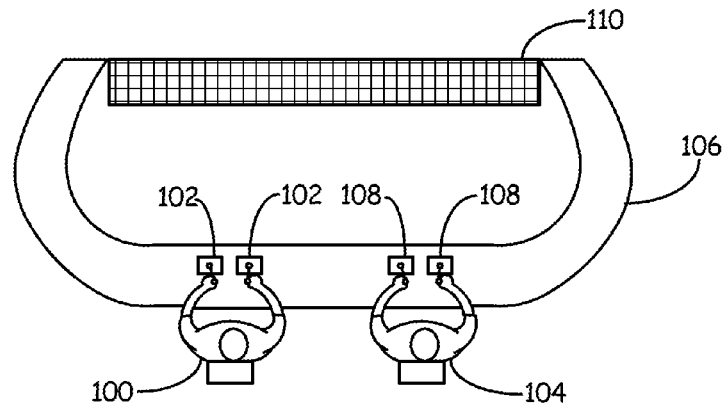
FIG. 3 is a perspective view of an exemplary surgeon console.

Referring to FIG. 3, a main surgeon 100 controls a pair of controls 102 while an assistant 104 working on the same surgeon console 106 or another surgeon console controls additional controls 108. The main surgeon 100 and/or the assistant 104 may also control various cameras. The main surgeon 100 and the assistant 104 can view the same display 110 or they may view separate displays, for example, showing different views of the patient. The display 110 may be a 2D display, a 3D display, a naked eye 3D display, or other type of suitable display. The assistant 104 may simultaneously operate and assist in the operation. Two or more operators may advantageously work on the same patient at the same time while maintaining dialog with each other. It will be appreciated that while a main surgeon and an assistant surgeon have been described, the console 106 may be operated by any one or two (or more) operators generically.

Figure 4:
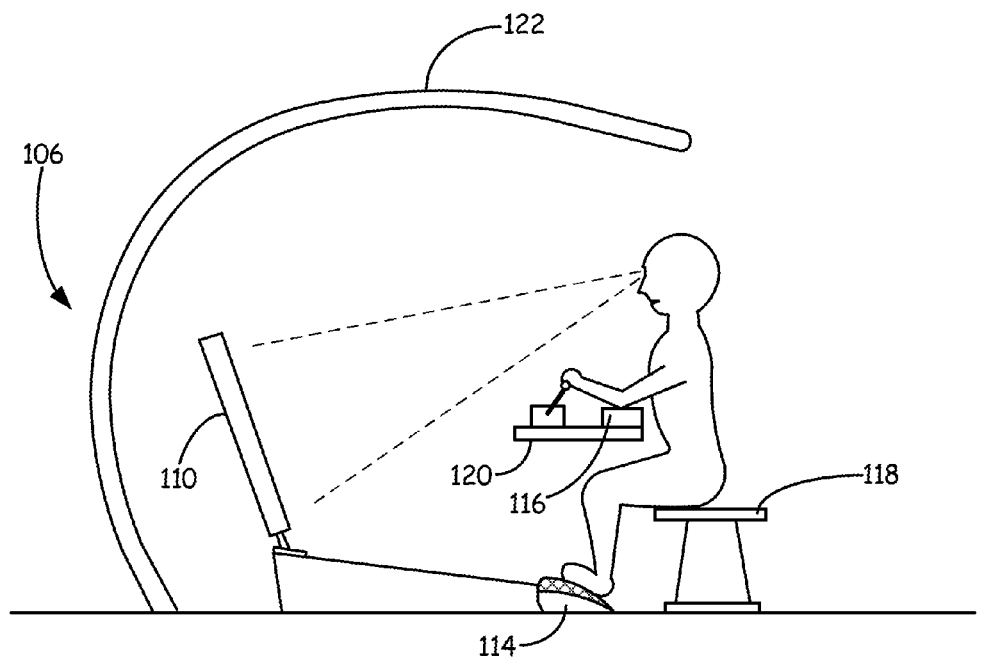
FIG. 4 is a side view of an exemplary surgeon console.

Referring to FIG. 4, the surgeon console 106 may be ergonomically arranged including one or more of the foot rest 114, the arm rest 116 and the seat 118. The foot rest 114 may incorporate switches to switch the controls 102 (and/or the controls 108) to control the camera instead of the manipulators/robots or vice-versa. The foot rest 114 may also incorporate controls to control manual focusing of the camera(s). The foot rest 114, arm rest 116, controls 102, controls 108 and/or any combination thereof may include sensors to detect the presence of the operator in order to enable/disable the robotic system.

The surgeon console 106 may also be arranged to avoid light reflection. For example, the display 110 may be positioned such that at least a portion is below a height of the table 120 at which the surgeon sits. The display 110 may also be angled such that reflections are not passed or reduced to the viewer at the table 120. The light shelter 122 may also be provided to reduce ambient lighting that may could cause reflections.

Haptic feedback may be provided to the main surgeon 100 and/or the assistant 104. A resisting force may be measured by the in-vivo robotic manipulator 2, for example via an onboard sensor such as a load cell. The resisting force may also be estimated from an amount of energy (e.g., voltage, current or power) used by the manipulator 2. Force feedback based on the resisting force may be provided to the main surgeon 100 and/or the assistant 104 via the manipulators 102 and 108 respectively.

Figure 5:
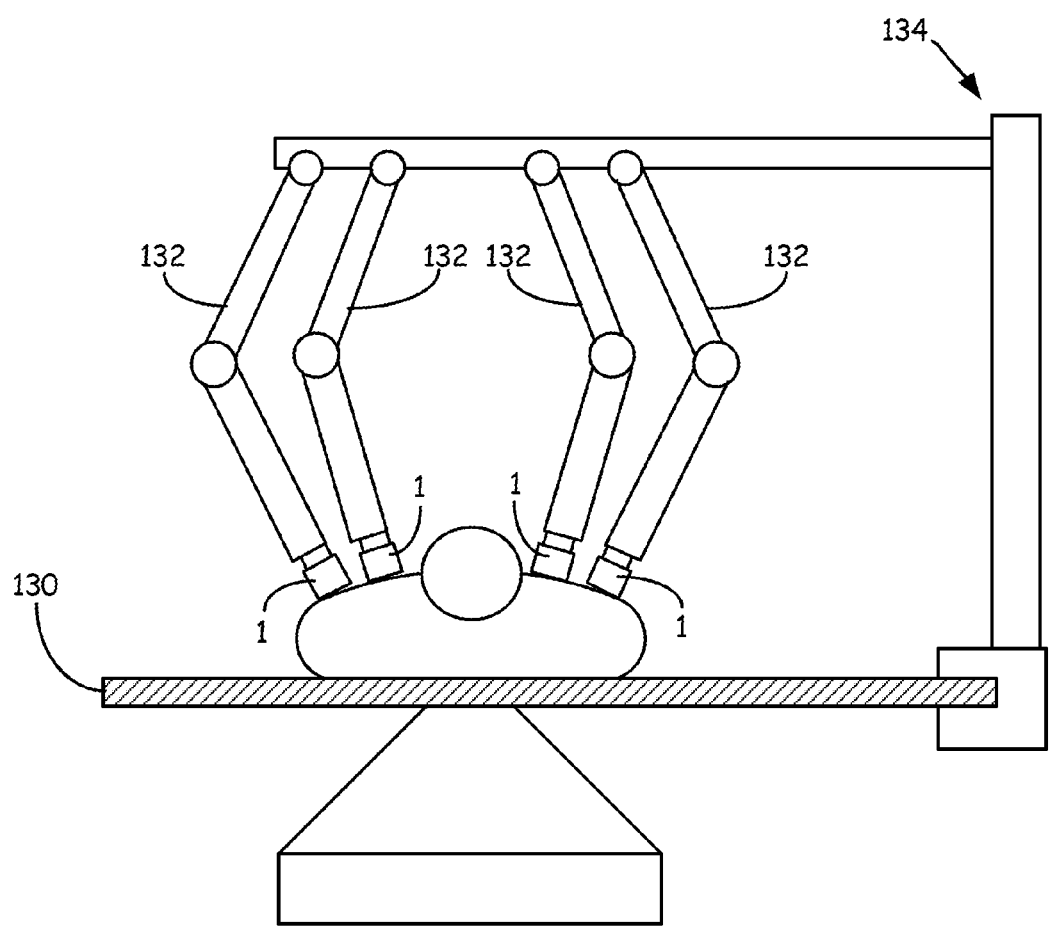
FIG. 5 is a side view of an exemplary patient table.

Referring to FIG. 5, an exemplary patient table 130 is shown. A plurality of the electromagnetic location fixing devices 1 may be coupled to arms 132. The arms 132, may be secured or coupled to the gantry 134, which is secured or coupled to the table 130. Thus, the whole system may move simultaneously with the patient. This allows for the changing of the position of the patient intra-operatively without the need to undock the robotic system from the patient and operations that require changes in patient position during the surgical procedure are facilitated. Also, the arms 132 may be servo driven for repositioning or adjusting an orientation of the electromagnetic location fixing devices 1.

Referring to FIGS. 6A and 6B, the axis of movement of the micro robotic manipulator 2 may have several different types of configurations. In the example shown in FIGS. 6A and 6B, 7-axis movement is shown. The joint 13 can rotate along the axes I and II, and the arm 14 can translate along direction III. The wrist 15 can rotate along axis IV, bend along axis V and bend along axis VI. A gripper/end effector 16 may also open and close along the axis VII, which could include rotational and/or translational movement. A portion of the micro robotic manipulator 2 having a joint with rotational axis similar to that of joint 13 and axes I and 2 as shown in FIG. 6 is referred to as Type A as a matter of convenience and is non-limiting.

FIGS. 7A and 7B show another configuration of the 7-axis movement of the manipulator 2 in which joint 13 rotates along axis I in another direction. A portion of the micro robotic manipulator 2 having a joint with rotational axis similar to that of joint 13 and axes I and II as shown in FIG. 7 is referred to as Type B as a matter of convenience and is non-limiting.

The enclosure of the manipulator 2 may facilitate the insertion of the manipulator into the body and protect the robotic arm and end effector inside the manipulator during insertion. It may include a base 21 and a pair of foldable flaps 17 on both sides of the base 21. As a non-limiting example, the flaps 17 may have a maximum diameter of 18 mm in a folded configuration. A maximum diameter of 18 mm is advantageous as it works well with an entrance port sized for use with most natural orifices.

During an initial state or insertion, the flaps are folded as shown in FIG. 8. Before deployment of the robot arm or end effector, the flaps 17 may be unfolded by a magnetic force triggered from the corresponding electromagnetic location fixing device 1.

The unfolding of the flaps 17 may be triggered by heat of the abdominal wall, by external radiation or by externally supplied power. For example, the base 21 may include a heating device activated by the supply of electrical current or by reception of a radiative energy from a transmitter included in the electromagnetic location fixing device 1. During removal from the body the flaps 17 may refold by cooling. The cooling may be effected by removing the electrical current or transmitted radiation supplied to the heating device and/or separating the manipulator 2 from the abdominal wall. The heating and cooling can also be achieved by other methods such as a thermo-electric heater/cooler, heat pipes, etc. This operation may be reversed with folding being triggered by heating and unfolding being triggered by cooling.

Alternatively or in addition, the flaps 17 may be a laminate of two materials having different coefficients of thermal expansion. Thus, as the flaps 17 are heated and cooled, the materials expand and contract at different rates causing the flaps 17 to fold and unfold. The materials may be metal alloys. The flaps 17 may be constructed from a shape memory alloy.

Alternatively or in addition, following the operation, the flaps 17 may be re-folded by manipulating the flaps 17 using another manipulator.

Alternatively or in addition, the flaps 17 may have a spring effect to assist in opening or closing the flaps and holding the flaps folded. For example, the flaps 17 may have a spring effect with a resultant force that tends to fold the flaps 17. In the presence of the fixing device 1, the spring effect is not strong enough to hold the flaps 17 folded and the flaps 17 are unfolded by the magnetic force. When the fixing device 1 is removed, the spring effect may cause the flaps 17 to fold.

Depending on the condition of the abdominal wall, translation motion of the flaps 17 may be provided by rollers on the flaps 17 (for example as shown by flaps 24 in FIG. 18) that are magnetically switchable or electrically actuatable.

Translation motion of the manipulator 2 may be provided by electromagnetic levitation. For example, the attractive force between the manipulator 2 and the electromagnetic location fixing device 1 may be lessened or reversed to permit movement with respect to the abdominal wall. The electromagnetic location fixing device 1 may then be moved on the abdominal wall by a servo or magnetic transport (similar to the electromagnetic fixing device 26 and base 25 shown in FIG. 18).

In the case of magnetic transport, magnets may be provided in the electromagnetic location fixing device 1. An externally supplied magnetic field is supplied to interact with the magnets of the electromagnetic location fixing device 1 or 26 to cause the electromagnetic location fixing device 1 to move in an X-Y direction and be repositioned with respect to the abdominal wall.

Figure 12:
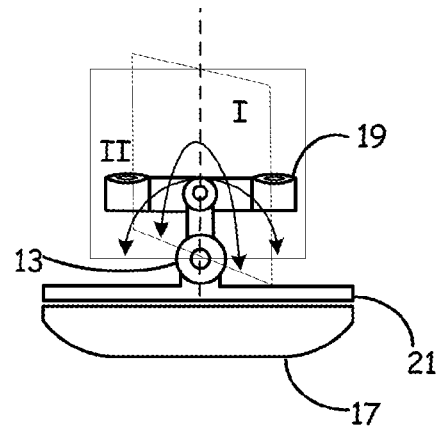
FIG. 12 is a side view showing 2-axis movement of an exemplary 3D micro robotic camera.
Figure 13:
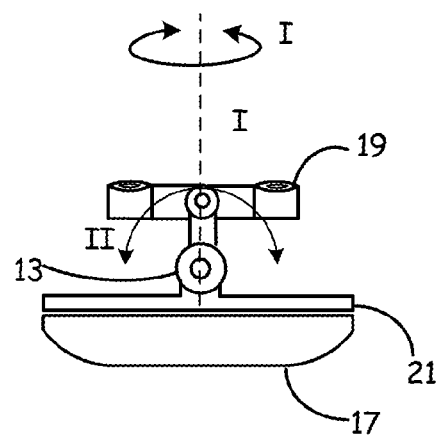
FIG. 13 is a side view showing 2-axis movement of an exemplary 3D micro robotic camera.
Figure 14A:
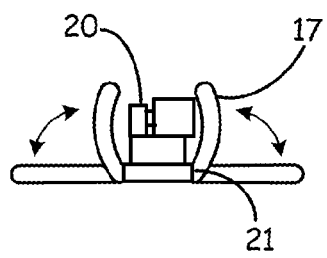
FIG. 14A is an end view and FIG. 14B is a side view of an exemplary foldable enclosure of a micro robotic 3D-camera.
Figure 14B:
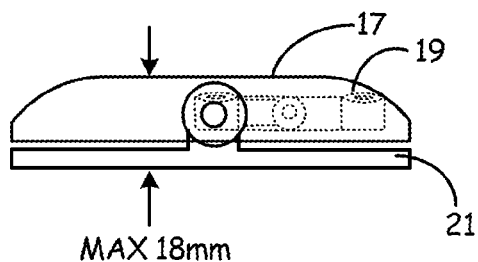

Depending on the purpose of the manipulator during operation, the end effector of the manipulator 2 may be adapted to a gripping device 16, an imaging device, such as a 2D video camera 18 or a 3D stereoscopic video camera 19, or other devices. In the case of a 2D or 3D camera, the camera may rotate along two perpendicular axes to acquire a 2D planar or 3D stereoscopic view in different orientations. Examples of two different types of configurations are shown in FIGS. 9 and 12 (Type A) and FIGS. 10 and 13 (Type B). The enclosure of the camera may facilitate the insertion of the manipulator into the body and protect the 2D camera or 3D camera inside the manipulator during insertion. During initial state or insertion of the 2D or 3D camera, the flaps are folded as shown in FIG. 11 and FIG. 14 respectively. As a non-limiting example, the flaps may have a maximum diameter of 18 mm. A maximum diameter of 18 mm is advantageous us as it works well with an entrance port sized for use with most natural orifices. Before deployment of the 2D camera, the flaps 17 are unfolded by a magnetic force triggered from the corresponding remotely controlled electromagnetic location fixing device 1. A spring loaded rotational joint 20 may be included for a 3D camera, as shown in FIG. 13.

Figure 15:
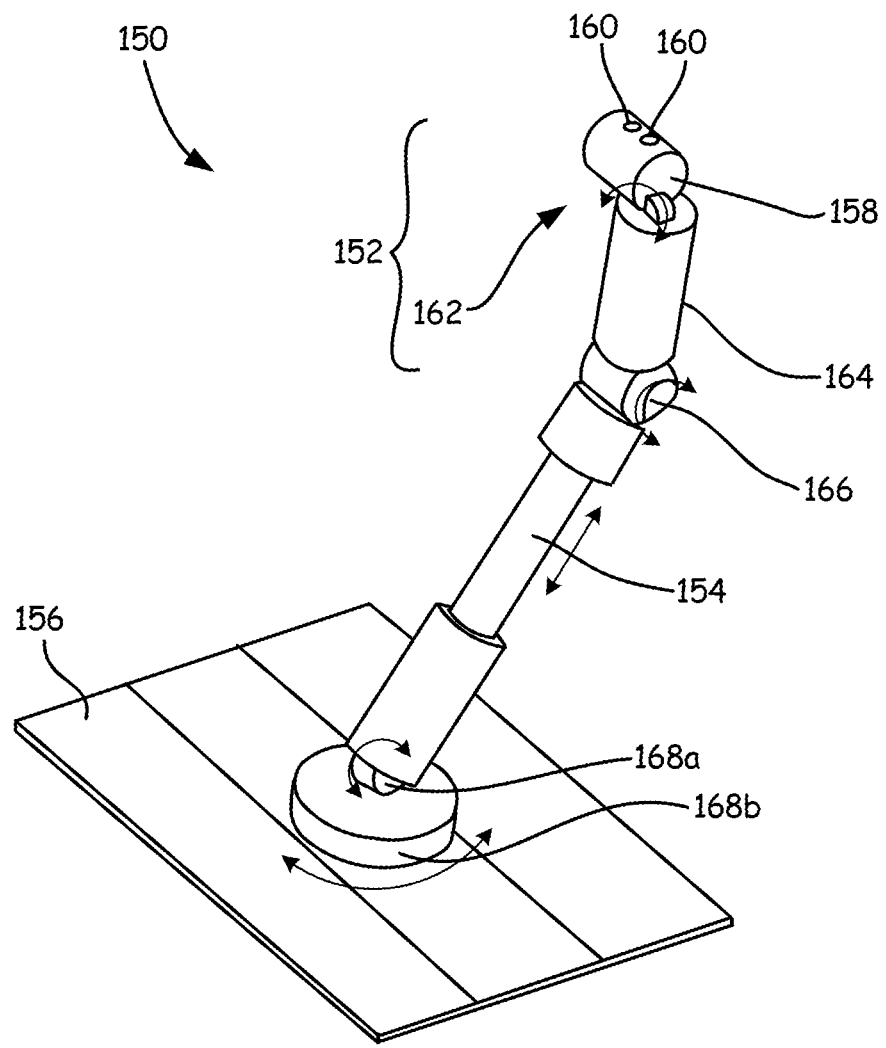
FIG. 15 is a perspective view of an exemplary 3D micro robotic camera.
Figure 16A:
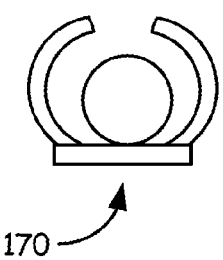
FIG. 16A is an end view of an exemplary micro robotic actuator in a folded configuration.
Figure 16B:
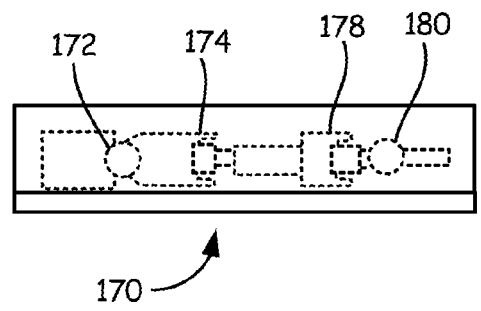
FIG. 16B is a side view of an exemplary micro robotic actuator in a folded configuration.
Figure 16C:
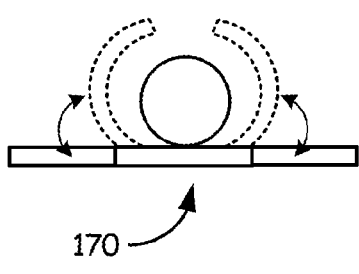
FIG. 16C is an end view of an exemplary micro robotic actuator in an unfolded configuration.
Figure 16D:
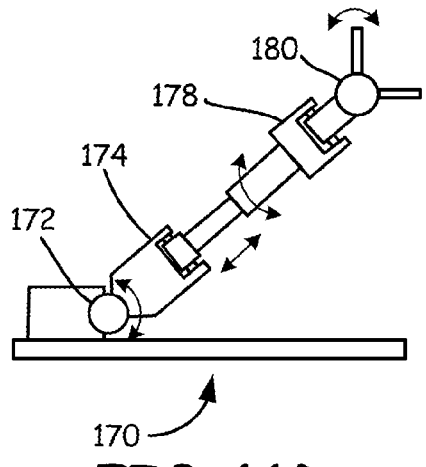
FIG. 16D is a side view of an exemplary micro robotic actuator in an unfolded state.

FIG. 15 is a perspective view of an exemplary 3D camera 150. The camera 150 may include 3 parts: a camera body 152, an extendable linkage bar 154 and a foldable magnetic anchorage 156. The camera body 150 may include a swivel head 158 and two camera lenses 160. The camera lenses 160 may be spaced apart along a major axis of the swivel head 158 and provide a 3D image. The major axis of the swivel head may coincide with a longitudinal axis of the camera 150 in its folded configuration. Spacing the camera lens along the longitudinal axis or "side" accommodates both of the camera lenses 160, thereby providing 3D imagery not otherwise possible, in the limited diameter available in the implantable device. When a forward looking view is needed, the swivel head 158 can swing approximately 90 degrees (or more) to allow the "side" looking cameras to look forward.

A flexible linkage 162, which may be a hinge, is linked to a body part 164, which may be a tube or tube-like control unit. The body part 164 is linked to the extendable linkage bar 154 via a flexible linkage 166, which may be a hinge. The extendable linkage bar 154 extends and retracts to allow positioning of the camera body 152 near to the surgical field. An opposite end of the extendable linkage bar 154 is linked, and in some cases locked, to the foldable magnetic anchorage 156, for example, through a 2-axis flexible linkage 168a and 168b. The flexible linkages 162, 166, 168a and 168b may be servo driven. The foldable magnetic anchorage 156 may be secured on the abdominal/body wall, for example by activating an external magnet or positioning a permanent magnet outside the abdominal wall.

The flexible linkages 162 and 166 allow the camera 150 to bend and position in difficult and confined spaces while being secured by the anchorage 156. The foldable magnetic anchorage 156 may also be swiveled slightly with a center of rotation at the abdominal wall, for example by swiveling the external magnetic anchor, to facilitate slight sideway movement of the camera for clearer vision of an area of interest.

FIG. 16 show an exemplary micro robotic actuator 170 having 7 degrees of freedom and multiple axis of movement provided by the joints 172, 174, 178 and 180.

Additional anchoring force may be provided to the electromagnetic location fixing device 1. For example, for an obese patient with a thick abdominal wall (e.g., 50 mm thick or more), it may be difficult to sufficiently secure the electromagnetic location fixing device 1 to the manipulator 2 for precise motion during a surgical procedure. It is important that a stable platform be provided for secure anchorage of the miniature robots. Also, space available to accommodate the manipulators 2 having a small profile is limited. Thus, providing for external actuation may be desirable to provide sufficient torque for seven full axes of movement in the gripping and moving of organs or tissues during a surgical operation.

Figure 19:
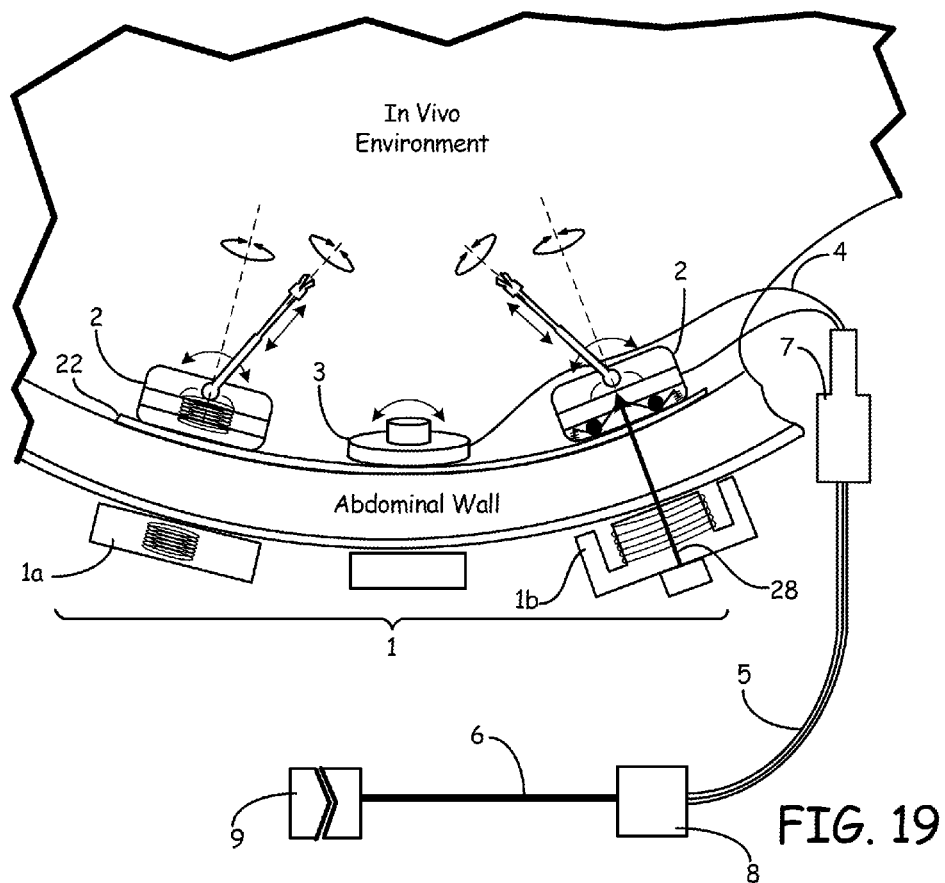
FIG. 19 is a schematic view of an exemplary surgical robotic system including a fine metal wire.
Figure 20A:
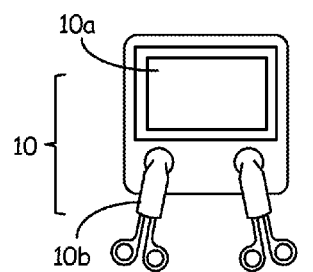
FIGS. 20A and 20B are front views of exemplary human machine interfaces.
Figure 20B:
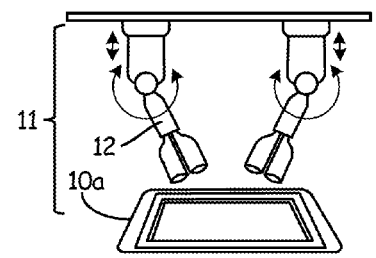
Figure 21:
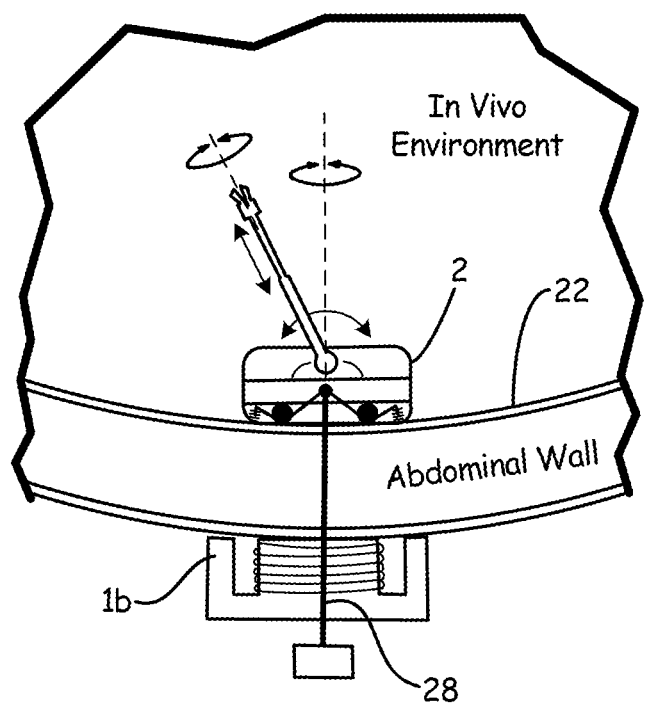
FIG. 21 is a side view showing insertion of an exemplary fine metal wire.

Referring to FIGS. 19 and 21, a flexible or semi-flexible magnetic sheet 22 can be inserted into the body cavity through the entrance port 7. When inserted, the magnetic sheet 22 may be rolled or folded. Once inserted, it can be unfolded or unrolled and positioned along the abdominal wall. The magnetic sheet 22 may be unfolded/unrolled by a mechanical mechanism or it may be unfolded/unrolled by subjecting it to a magnetic field, which may be supplied by an external electromagnet, and/or by heating or cooling through supplied energy.

The magnetic sheet 22 may be provided as a single large sheet sufficient to cover a large area of the inner abdominal wall. The magnetic sheet may also be provided by one or more small or medium sized sheets to provide coverage for a certain region of the abdominal wall.

Figure 28:
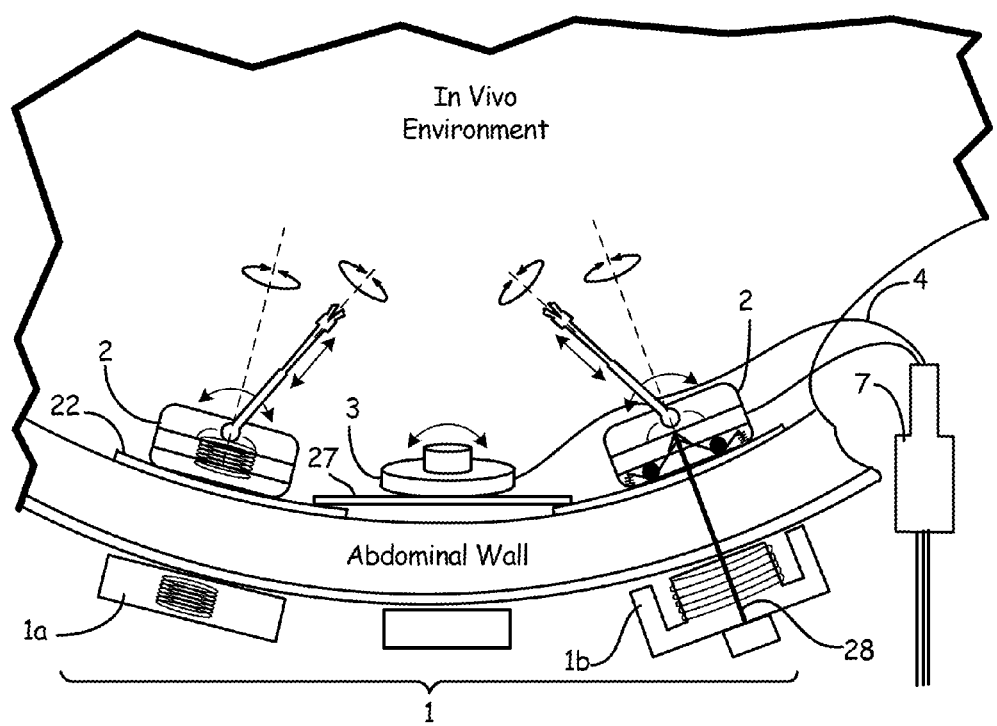
FIG. 28 is side view of an exemplary intra abdominal mechanical frame.

An intra abdominal mechanical frame, for example the intra abdominal mechanical frame 27 shown in FIG. 28, may be constructed by linking individual magnetic sheets with extendable bars to provide a stable platform for the miniature robots to operate. This intra abdominal mechanical frame may, in some cases, provide anchoring support similar to that of a large flexible magnetic sheet covering a large part of the abdomen without requiring the use of such a large sheet.

The position of the magnetic sheet 22 may be fixed by the external electromagnet 1b. The magnetic sheet 22 provides a stable platform for the micro robotic manipulator 2 to attach to. The magnetic sheet 22 may provide a medium to concentrate magnetic flux and provide for the secure anchorage of micro robotic manipulators such as the micro robotic manipulator 2. Exemplary materials that provide such a medium to concentrate flux include iron and silicon-iron based materials. It will be appreciated that this secure anchorage can be provided for any micro robotic manipulator as well as other related devices such as a camera. It will also be appreciated that the magnetic sheet may be used with, but is not required for, any of the described examples including those of FIGS. 1 and 17-28.

To provide additional anchorage force, a fine wire 28 may be included. The fine wire 28, which may be a metal wire, extends from the external electromagnet 1b and may be introduced through the abdominal wall via, or in the form of, a fine needle. To facilitate introduction of the fine metal wire 28 via a needle or hypodermic syringe, the wire 28 may have a maximum diameter of 1 mm. A maximum diameter of 1 mm is preferable so that punctures remain well below a size that would be regarded an incision and leave no significant visible scarring. It will be appreciated that other materials such as flexible or rigid fibers, biocompatible polymers/plastics and multi-material composites that may or may not include a metal may be used in place of metal for the wire 28.

As an example, the fine metal wire 28 may be provided from the external electromagnet 1b via a circular through hole, a slot, or another aperture in the electromagnet 1b. The hole, slot or other aperture may be provided at a center of the electromagnet 1b.

A locking mechanism, such as a pair of inclined metal tabs having a separation less than a thickness of the fine wire 28 or a tip thereof, may be provided to releasably lock the micro manipulator 2 on the tip of the fine wire 28. In the example of a locking mechanism using a metal tab, the metal tab may be subject to a biasing force, such as a spring, to keep the fine wire 28 locked in the micro robotic manipulator 2. Removing the biasing force or providing a counter force may allow the fine wire 28 to be released. The release of the fine wire 28 may be provided by a remote controlled electrical actuator or by mechanical action, for example by an endoscope, inside the abdomen.

Figure 22:
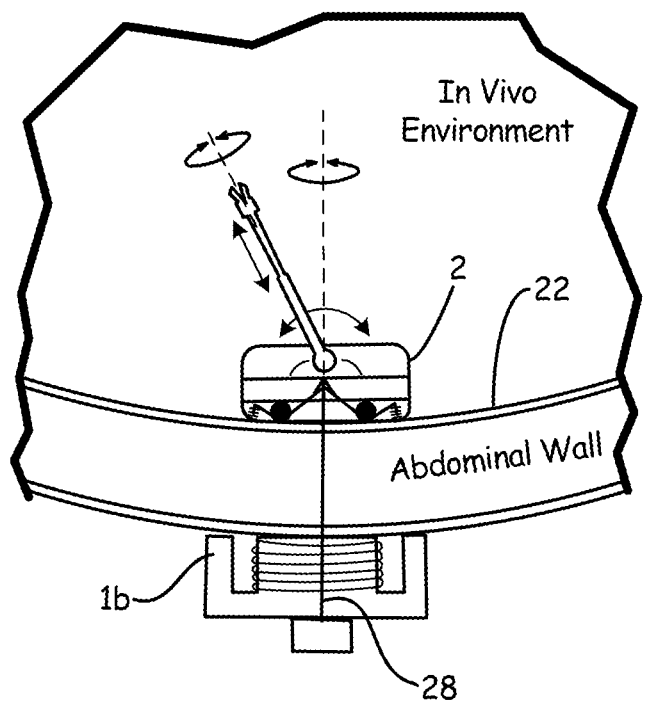
FIG. 22 is a side view showing locking of an exemplary fine metal wire to a miniature robot.

Referring to FIG. 22, the tip of the metal wire 28 may be locked by a releasable non-return mechanism. The tip of the fine wire 28 may be enlarged to provide a more secure lock.

Figure 23:
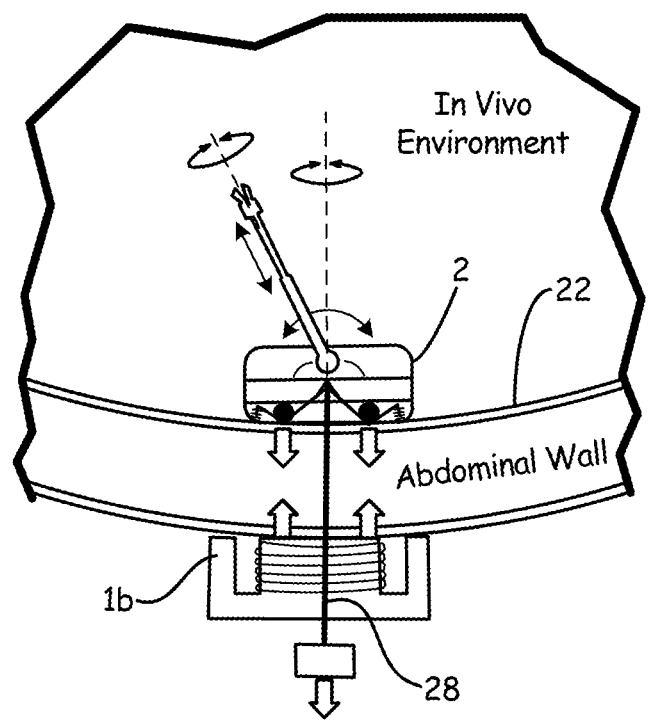
FIG. 23 is a side view showing an example of force of tightening by a fine metal wire.
Figure 24:
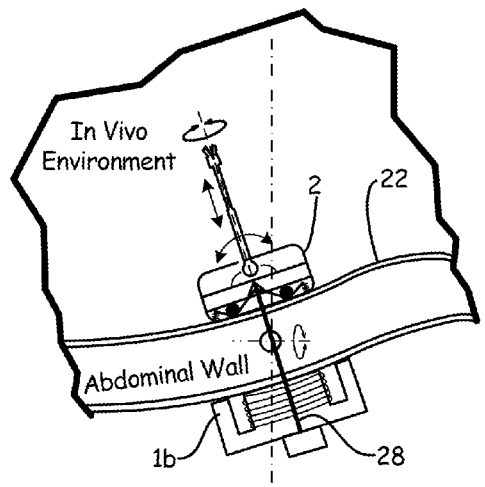
FIG. 24 is a side view showing exemplary X-Y movement of a micro robotic manipulator to the left with a fine metal wire.
Figure 25:
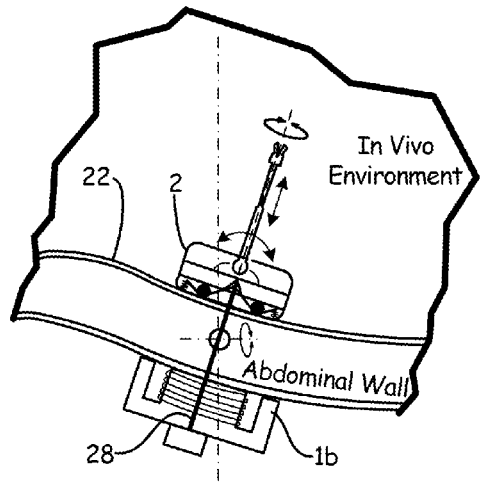
FIG. 25 is a side view showing exemplary X-Y movement of a micro robotic manipulator to the right with a fine metal wire.
Figure 26:
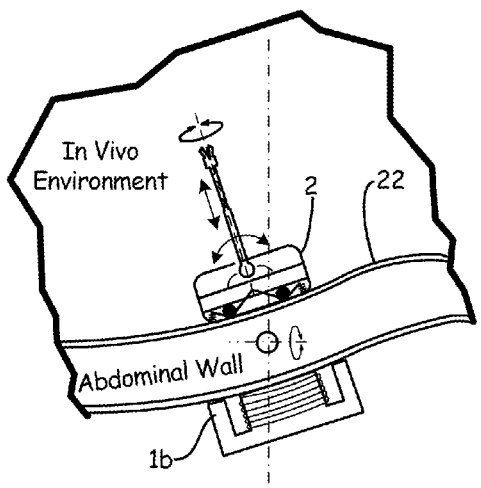
FIG. 26 is a side view showing exemplary X-Y movement of a micro robotic manipulator to the left without a fine metal wire.
Figure 27:
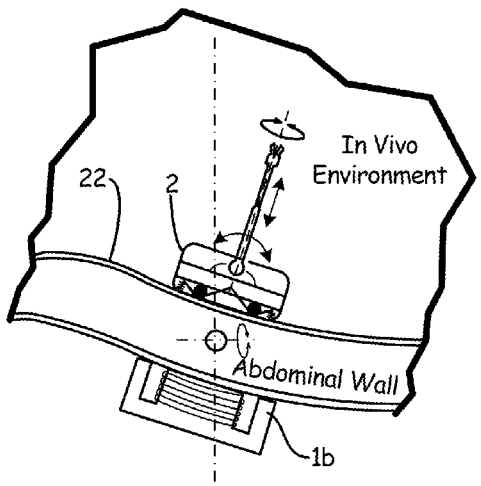
FIG. 27 is a side view showing exemplary X-Y movement of a micro robotic manipulator to the right without a fine metal wire.

Referring to FIG. 23, when the fine wire 28 is tightened at the base of the external electromagnet 1b, the external electromagnet 1b and the miniature robot 2 are pressed against the abdominal wall from opposite sides such that an additional locking force is provided for the micro robotic manipulator 2 to attach to the stable platform. Therefore, secure and stable movements of the micro robotic manipulator 2 are provided in carrying out the surgical operation.

An aperture may be provided in the external electromagnet 1b through which the fine wire 28 passes. The aperture may be in the form of a slot, a cross, a large singular opening, or another shape. Providing the aperture allows for the relocation of the micro robotic manipulator 2 after the fine wire 28 has been inserted in the abdominal wall without requiring a reinsertion of the fine wire 28. Thus, the wire may be loosened allowing the movement of the external electromagnet 1b and the micro robotic manipulator 2 and subsequently retightened to allow for the repositioning of the micro robotic manipulator 2.

In addition to providing additional anchorage force, the fine wire 28 may also be used to supply power or signals to/from the micro robotic manipulator 2.

Referring to FIGS. 24-27, when the miniature robot is tightly coupled to the electromagnet, movement of the micro robotic manipulator 2 may be induced by the swivel action of external electromagnet 1b. For example, the center of movement may be located at the midpoint of the abdominal wall.

The external actuation can supplement the X-Y movement of micro-actuator on the micro robotic manipulator 2. Due to the leverage effect, a small angular movement of the electromagnet 1b will lead to a large two dimensional X-Y movement of the micro robotic manipulator 2. Without the tight coupling, attempts to move the micro robotic manipulator 2 in this manner would likely result in separation of the micro robotic manipulator 2 and the external electromagnet 1b and X-Y movement would not be achieved.

Although the above described provision of additional anchorage force has been described in the context of a micro robotic manipulator and an external magnet, it will be appreciated that this is merely an exemplary application and the described apparatus and methods can also be applied to any of a variety of other instruments in which anchorage onto a stable platform inside a body cavity is desired.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages. In particular, and unless otherwise stated, the various features and aspects of the described embodiments may be used separately and/or interchangeably in any combination and are not limited to the arrangements described above.

Additionally, the section headings herein are provided for consistency with the suggestions under 37 C.F.R. 1.77 or otherwise to provide organizational cues. These headings shall not limit or characterize the invention(s) set out in any claims that may issue from this disclosure. Specifically and by way of example, a description of a technology in the "Background" is not to be construed as an admission that technology is prior art to any invention(s) in this disclosure. Neither is the "Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

The invention claimed is:

1. A surgical system, comprising:
an external anchor adapted to be positioned outside a body and adapted to generate a selectively controllable magnetic field;
an entrance port adapted to be secured through an abdominal cavity of the body; and
an internal anchor comprising an instrument and a foldable flap, the internal anchor adapted to be inserted into the body via the entrance port, the internal anchor positioned inside the body, the foldable flap transitionable between a normally folded position and an unfolded position by selectively controlling an application of the magnetic field generated by the external anchor, the foldable flap configurable to transition to the unfolded position to magnetically couple the internal anchor with the external anchor based on the selective controlling of the magnetic field generated by the external anchor;
wherein the magnetic field of the external anchor is configured to facilitate repositioning of the internal anchor;
wherein the external anchor is adapted to selectively control the generated magnetic field based in part upon a repelling force provided between the internal anchor and external anchor to increase a separation distance between the internal anchor and the external anchor prior to repositioning of the internal anchor;
wherein the instrument comprises an elongated structure having a first end and a second end;
wherein the first end comprises an end-effector and a wrist securing the end-effector to the first end, the end-effector having multiple degrees of movement via multiple axes, the wrist allowing the end-effector to rotate about an axis independent from the multiple axes; and
wherein the second end is secured to the internal anchor by a rotatable joint.

2. The surgical system of claim 1, further comprising a flexible magnetic sheet adapted for insertion into the body via the single entrance port, wherein the magnetic sheet is adapted to unfold or unroll and refold or roll in the presence of a magnetic field.

3. The surgical system of claim 2, wherein the magnetic sheet is adapted to unfold or unroll and refold or roll by heating or cooling.

4. The surgical system of claim 2, wherein positioning the magnetic sheet between the external anchor and the internal anchor concentrates magnetic flux between the external anchor and the internal anchor thereby increasing a coupling force between the external anchor and the internal anchor.

5. The surgical system of claim 2, further comprising a second flexible magnetic sheet adapted for insertion into the body via the single entrance port, wherein the two flexible magnetic sheets are linkable with extendable bars to form an intra-body mechanical frame.

* * * * *